US010082490B1

(12) United States Patent
Prakash et al.

(10) Patent No.: US 10,082,490 B1
(45) Date of Patent: Sep. 25, 2018

(54) VARIABLE DATA-DEPENDENT ACQUISITION AND DYNAMIC EXCLUSION METHOD FOR MASS SPECTROMETRY

(71) Applicants: Thermo Finnigan LLC, San Jose, CA (US); Amol Prakash, Shrewsbury, MA (US)

(72) Inventors: Amol Prakash, Shrewsbury, MA (US); Scott M. Peterman, Grimes, IA (US); David Sarracino, Belmont, MA (US)

(73) Assignee: Thermo Finnigan LLC, San Jose, CA (US)

( * ) Notice: Subject to any disclaimer, the term of this patent is extended or adjusted under 35 U.S.C. 154(b) by 0 days.

(21) Appl. No.: 15/898,901

(22) Filed: Feb. 19, 2018

Related U.S. Application Data

(63) Continuation of application No. 15/498,114, filed on Apr. 26, 2017, now Pat. No. 9,897,581.

(51) Int. Cl.
*H01J 49/00* (2006.01)
*G01N 30/72* (2006.01)
(Continued)

(52) U.S. Cl.
CPC ......... *G01N 30/7233* (2013.01); *G01N 33/50* (2013.01); *G01N 2560/00* (2013.01);
(Continued)

(58) Field of Classification Search
CPC ............... G01N 30/7233; G01N 33/50; G01N 2560/00; H01J 49/425; H01J 49/0031; H01J 49/0045
(Continued)

(56) References Cited

U.S. PATENT DOCUMENTS

| 7,498,568 B2 | 3/2009 | Overney et al. |
| 7,880,136 B2 | 2/2011 | Makarov et al. |

(Continued)

FOREIGN PATENT DOCUMENTS

| WO | WO2007030948 A1 | 3/2007 |
| WO | WO2016011355 A1 | 1/2015 |

(Continued)

OTHER PUBLICATIONS

Egertson et al., "Multiplexed MS /MS for improved data independentacquisition", Nature Methods, 2013, vol. 10 (8), pp. 744-748.

*Primary Examiner* — Michael Maskell
(74) *Attorney, Agent, or Firm* — Charles B. Katz

(57) ABSTRACT

A variable data dependent acquisition/dynamic exclusion (vDDA/DE) method selects target m/z range utilizing a MS1 precursor topography map over the most recently acquired MS spectrum to identify the precursor m/z values and MS/MS acquisition parameters to improve the selection of the next data-dependent MS/MS acquisition. The topography used to define the next set of DDA scan events is defined by previous tandem MS scan events defined by precursor quadrupole isolation windows as well as all detected compounds contained within the specific tandem MS events. At least some of the parameters used for MS/MS data acquisition are dynamic so as to exhaustively sample the user specified MS mass range with MS/MS information. These parameters include the quadrupole MS isolation width and symmetry around the targeted m/z value. Using this approach, a greater proportion of the precursor m/z space is effectively and efficiently sampled per chromatographic peak width.

22 Claims, 10 Drawing Sheets

(51) Int. Cl.
  *G01N 33/50* (2006.01)
  *H01J 49/42* (2006.01)
(52) U.S. Cl.
  CPC ....... *H01J 49/0031* (2013.01); *H01J 49/0045* (2013.01); *H01J 49/425* (2013.01)
(58) Field of Classification Search
  USPC .............................................. 250/281, 282
  See application file for complete search history.

(56) References Cited

U.S. PATENT DOCUMENTS

| | | |
|---|---|---|
| 8,809,770 B2 | 8/2014 | Bonner et al. |
| 8,809,772 B2 | 8/2014 | Bonner et al. |
| 8,847,152 B2 | 9/2014 | Scigocki |
| 9,202,677 B2 | 12/2015 | Tate et al. |
| 2012/0261568 A1 | 10/2012 | Coon et al. |
| 2013/0153761 A1* | 6/2013 | Bonner ............... H01J 49/0031 250/282 |
| 2016/0005581 A1 | 1/2016 | Graichen et al. |

FOREIGN PATENT DOCUMENTS

| | | |
|---|---|---|
| WO | WO2015068001 A1 | 5/2015 |
| WO | WO2015097504 A1 | 7/2015 |

\* cited by examiner

Precursor Isolation
- 2 Da
– 5 Da
— 10 Da
— 15 Da

Maximum Ion Fill Times
— 30 msec
— 80 msec
— 150 msec

AGC Target Value
⤋ 5e4
╋ 1e5
⤊ 5e5

VARIABLE DATA-DEPENDENT ACQUISITION AND DYNAMIC EXCLUSION METHOD FOR MASS SPECTROMETRY

CROSS-REFERENCE TO RELATED APPLICATIONS

The present application is a continuation under 35 U.S.C. § 120 and claims the priority benefit of co-pending U.S. patent application Ser. No. 15/498,114, filed Apr. 26, 2017. The disclosure of the foregoing application is incorporated herein by reference.

FIELD OF THE INVENTION

The invention relates generally to mass spectrometry, and more particularly to automated acquisition of tandem mass spectrometry (MS/MS and MS") spectra utilizing data-dependent methodologies.

BACKGROUND

Data-dependent acquisition (DDA) (also referred to, in various commercial implementations, as Information Dependent Acquisition, Data Directed Analysis, and AUTO MS/MS) is a valuable and widely-used tool in the mass spectrometry art, particularly for the analysis of complex samples. Generally described, data-dependent acquisition involves using data derived from an experimentally-acquired mass spectrum in an "on-the-fly" manner to direct the subsequent operation of a mass spectrometer; for example, a mass spectrometer may be switched between MS and MS/MS scan modes upon detection of an ion species of potential interest. Utilization of data-dependent acquisition methods in a mass spectrometer provides the ability to make automated, real-time decisions in order to maximize the useful information content of the acquired data, thereby avoiding or reducing the need to perform multiple chromatographic runs or injections of the analyte sample. These methods can be tailored for specific desired objectives, such as enhancing the number of peptide identifications from the analysis of a complex mixture of peptides derived from a biological sample.

DDA methods may be characterized as having one or more input criteria, and one or more output actions. The input criteria employed for conventional data-dependent methods are generally based on parameters such as intensity, intensity pattern, mass window, mass difference (neutral loss), mass-to-charge (m/z) inclusion and exclusion lists, and product ion mass. The input criteria are employed to select one or more ion species that satisfy the criteria. The selected ion species are then subjected to an output action (examples of which include performing MS/MS or MS" analysis and/or high-resolution scanning) In one instance of a typical data-dependent experiment, a group of ions are mass analyzed, and ion species having mass spectral intensities exceeding a specified threshold are subsequently selected as precursor ions for MS/MS analysis, which may involve operations of isolation, dissociation of the precursor ions, and mass analysis of the product ions.

Current DDA methods are target specific and utilize the targeted precursor m/z value to direct product ion acquisition around a narrow isolation width as well as creation of dynamic exclusion (DE) values. In addition, existing DDA methods generally use static tandem mass spectral acquisition parameters (e.g., automatic gain control (AGC) target value, maximum ion fill times, resolution, etc.). This method achieves positive outcomes for MS/MS spectrum identification, but penalizes the MS/MS coverage and limits the precursor mass range coverage.

In translational/clinical research, the goal is to perform global protein profiling on a targeted proteome to identify, verify (sequencing), and quantify potential marker panels. This requires robust, accurate, and reproducible experimental liquid chromatography-mass spectrometry (LC-MS) and MS/MS data acquisition, enabling qualitative and quantitative analysis of all compounds in the biological mixture repetitively across all biological samples that are analyzed in a study. In addition, the resulting data must facilitate retrospective data mining to accommodate various hypotheses-based data processing on existing and yet-to-be determined/developed knowledge bases. These knowledge bases can be described as protein or peptide sequences, SNPs, as well as post-translational modifications.

One drawback that is associated with current DDA methods is that not all MS/MS information is available in every single injection, leaving information gaps which can make it impossible to assign a particular identification to a precursor recorded in the survey MS1 spectrum. This makes a retrospective data mining difficult, as a particular precursor of interest may be quantified from the MS1 trace, but no MS/MS information might be available for the identification/confirmation of that MS1 trace. Even with an improvement in the data analysis step using a so-called 'match-between-runs," which maps MS1 precursors across several injections to match the corresponding MS/MS information, the data set may still contain gaps that make the retrospective analysis of the data set incomplete.

It would therefore be beneficial to provide methods that overcome at least some of the above-mentioned disadvantages and/or limitations.

SUMMARY OF THE INVENTION

In accordance with an aspect of at least one embodiment there is provided a method for mass spectral analysis of a sample containing a plurality of biomolecule species, comprising repeatedly performing data-dependent acquisition cycles across a chromatographic elution peak, each data-dependent acquisition cycle including steps of: A) acquiring a survey MS1 scan extending across a mass range of interest of an ensemble of ions generated from a sample; B) selecting a plurality of precursor ions based on the acquired MS1 scan, the selected plurality of precursor ions excluding precursor ions selected in a previous data-dependent acquisition cycle; C) for each of the selected precursor ions, performing the following steps: i) determining a set of instrumental parameters for obtaining MS/MS spectra of a current selected precursor ion, the instrumental parameters determined at least partially based on the basis of a characteristic of a peak in the MS1 scan associated with the current selected precursor ion, the set of instrumental parameters including an isolation window width; ii) obtaining a MS/MS spectrum corresponding to the current selected precursor ion using the determined instrumental parameters for the current selected precursor ion, wherein the MS/MS spectrum is acquired using an isolation window having the determined isolation window width, wherein the isolation windows cover, in the aggregate, across at least 70% of the mass range of interest.

In accordance with an aspect of at least one embodiment there is provided a method for mass spectral analysis of a sample containing a plurality of biomolecule species, comprising repeatedly performing data-dependent acquisition cycles across a chromatographic elution peak, each data-dependent acquisition cycle including steps of: A) using a mass spectrometer, acquiring a MS1 spectrum of an ensemble of ions that is generated from a sample, the MS1 spectrum covering at least a mass-to-charge (m/z) range of interest; B) selecting a first plurality of precursor ions based on the acquired MS1 scan, each one of the selected precursor ions having a known m/z value within the m/z range of interest; C) for each selected precursor ion, determining a precursor isolation range having a width defined between upper and lower m/z limits that are both within the m/z range of interest, the width determined at least partially based on a characteristic of a spectral peak in the MS1 scan that is associated with the selected precursor ion, and the known m/z value of the selected precursor ion being within the precursor isolation range; wherein for at least one of the selected precursor ions the determined precursor isolation range has a first width and for at least another of the selected precursor ions the determined precursor isolation range has a second width that is different from the first width; wherein for at least one of the selected precursor ions a location of the known m/z value thereof is other than approximately mid-way between the upper and lower m/z limits of the determined precursor isolation range; and D) for each of the selected precursor ions, in sequence, performing an analysis comprising: i) controlling the mass spectrometer to isolate ions having m/z values within the precursor isolation range for a current selected precursor ion; ii) fragmenting the isolated ions; and iii) mass analyzing the fragmented isolated ions to generate a MS/MS spectrum of the isolated ions, wherein, in aggregate, the determined precursor isolation ranges of the selected first plurality of precursor ions cover at least 70% of the m/z range of interest.

In accordance with an aspect of at least one embodiment there is provided a non-transitory computer readable medium containing machine-readable program instructions for causing a controller to mass spectrally analyze a sample containing a plurality of biomolecule species by repeatedly performing data-dependent acquisition cycles across a chromatographic elution peak, each data-dependent acquisition cycle comprising the following steps: A) acquiring a survey MS1 scan extending across a mass range of interest of an ensemble of ions generated from a sample; B) selecting a plurality of target precursor ions based on the acquired MS1 scan, the selected plurality of precursor ions excluding precursor ions selected in a previous data-dependent acquisition cycle; C) for each of the selected target precursor ions, performing the following steps: i) determining a set of instrumental parameters for obtaining MS/MS spectra of a current target precursor ion, the instrumental parameters determined at least partially on the basis of a characteristic of a peak in the MS1 scan associated with the current target precursor ion, the set of instrumental parameters including an isolation window width; ii) obtaining a MS/MS spectrum corresponding to the current target precursor ion using the determined instrumental parameters for the current target precursor ion, wherein the MS/MS spectrum is acquired using an isolation window having the determined isolation window width; and wherein the isolation windows cover, in the aggregate, across at least 70% of the mass range of interest.

In accordance with an aspect of at least one embodiment there is provided a non-transitory computer readable medium containing machine-readable program instructions for causing a controller to mass spectrally analyze a sample containing a plurality of biomolecule species by repeatedly performing data-dependent acquisition cycles across a chromatographic elution peak each data-dependent acquisition cycle comprising the following steps: A) using a mass spectrometer, acquiring a MS1 spectrum of an ensemble of ions that is generated from a sample, the MS1 spectrum covering at least a mass-to-charge (m/z) range of interest; B) selecting a first plurality of precursor ions based on the acquired MS1 scan, each one of the selected precursor ions having a known m/z value within the m/z range of interest; C) for each selected precursor ion, determining a precursor isolation range having a width defined between upper and lower m/z limits that are both within the m/z range of interest, the width determined at least partially based on a characteristic of a spectral peak in the MS1 scan that is associated with the selected precursor ion, and the known m/z value of the selected precursor ion being within the precursor isolation range; wherein for at least one of the selected precursor ions the determined precursor isolation range has a first width and for at least another of the selected precursor ions the determined precursor isolation range has a second width that is different from the first width; wherein for at least one of the selected precursor ions a location of the known m/z value thereof is other than approximately mid-way between the upper and lower m/z limits of the determined precursor isolation range; and D) for each of the selected precursor ions, in sequence, performing an analysis comprising: i) controlling the mass spectrometer to isolate ions having m/z values within the precursor isolation range for a current selected precursor ion; ii) fragmenting the isolated ions; and ii) mass analyzing the fragmented isolated ions to generate a MS/MS spectrum of the isolated ions, wherein, in aggregate, the determined precursor isolation ranges of the selected first plurality of precursor ions cover at least 70% of the m/z range of interest.

In at least one embodiment, the problem of information gaps in MS/MS data sets is addressed by covering the MS/MS space using a more intelligent approach, in which the precursor isolation window is varied based on the MS1 precursor topology. A goal of the acquisition strategy is to maximize precursor sampling while maintaining global quantitation for comprehensive translational/clinical research support. This approach satisfies at least some of the following requirements, to effectively address the large-scale data requirements and support integration across laboratories performing translational/clinical research:

Ease of use

Maximizes breadth of component profiling via tandem MS

Maximizes depth of sampling (dynamic range)

Reproducible across all samples (pilot to large-scale validation studies)

Established data processing strategies

Facilitates retrospective data analysis

Amenable to UHPLC for throughput concerns

Robust method transfers

A method according to at least one embodiment is an extension of existing data dependent acquisition and dynamic exclusion (DDA/DE) methods. While the overall routine is similar to existing methods, embodiments of the present invention include two modifications relating to: (1) precursor target m/z range selection; and (2) determining corresponding tandem mass spectral acquisition parameters for analyzing each precursor target m/z range. Specifically, the target m/z range selection is modified by utilizing a MS1 precursor topography map over the most recently acquired MS spectrum to identify the precursor m/z values and MS/MS acquisition parameters to improve the selection of the next data-dependent MS/MS acquisition. The topography used to define the next set of DDA scan events is defined by previous tandem MS scan events defined by precursor quadrupole isolation windows as well as all detected compounds contained within the specific tandem MS events.

In essence at least some of the parameters used for MS/MS data acquisition are not static, as is the case in classical DDA acquisition, but are dynamic so as to exhaustively sample the user specified MS mass range with MS/MS information. These parameters include the quadrupole MS isolation width and symmetry around the targeted m/z value. Using this approach, a greater proportion of the precursor m/z space is effectively and efficiently sampled per chromatographic peak width.

BRIEF DESCRIPTION OF THE DRAWINGS

The instant invention will now be described by way of example only, and with reference to the attached drawings, wherein similar reference numerals denote similar elements throughout the several views, and in which.

DETAILED DESCRIPTION OF EMBODIMENTS OF THE INVENTION

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the scope of the invention. Thus, the present invention is not intended to be limited to the embodiments disclosed, but is to be accorded the widest scope consistent with the principles and features disclosed herein. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
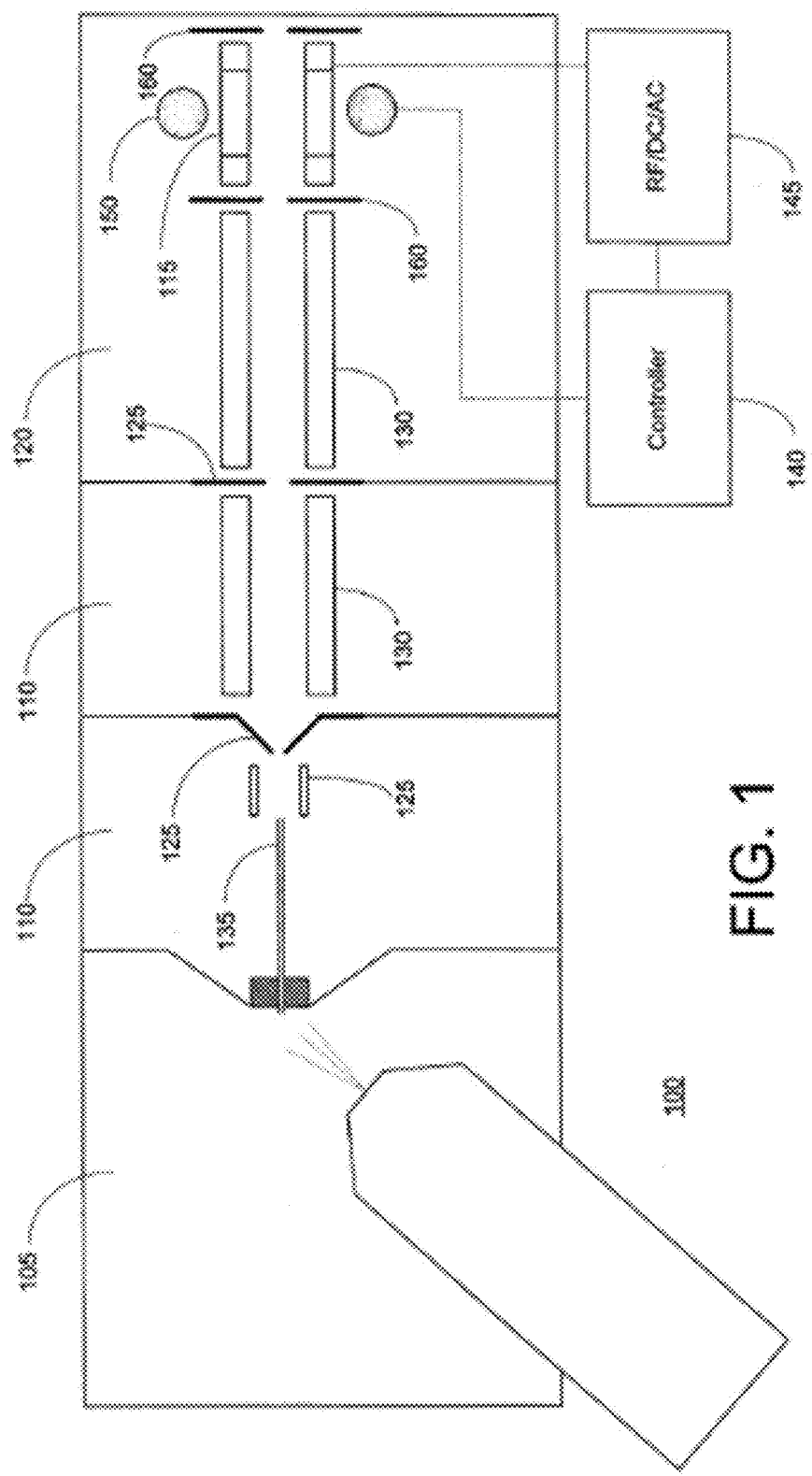
FIG. 1 is a schematic diagram of an exemplary mass spectrometer system, in which the variable data-dependent and dynamic exclusion (vDDA/DE) techniques according to embodiments of the present invention may be implemented.

FIG. 1 is a schematic depiction of a mass spectrometer 100 in which the data-dependent methods described herein may be beneficially implemented. It should be noted that mass spectrometer 100 is presented by way of a non-limiting example, and that the embodiments of the present invention may be practiced in connection with mass spectrometer systems having architectures and configurations different from those depicted herein. Ions are generated from a sample to be mass analyzed, such as the eluate from a liquid chromatographic column, by an ion source 105. Ion source 105 is depicted as an electrospray source, but may alternatively take the form of any other suitable type of continuous or pulsed source. The ions are transported through intermediate chambers 110 of successively lower pressure and are subsequently delivered to a mass analyzer 115 located in vacuum chamber 120. Various ion optical devices, such as electrostatic lenses 125, radio-frequency (RF) multipole ion guides 130, and ion transfer tube 135, may be disposed in the intermediate and vacuum chambers 110 and 120 to provide ion focusing and ion-neutral separation and thereby assist in the efficient transport of ions through mass spectrometer 100.

As shown in FIG. 1, mass analyzer 115 may take the form of a two-dimensional quadrupole ion trap mass analyzer similar to that used in the LTQ mass spectrometer available from Thermo Fisher Scientific Inc. (San Jose, Calif.). It is noted that ion trap mass analyzers (including the two-dimensional ion trap depicted and described herein as well as three-dimensional ion traps) are capable of performing mass analysis, precursor isolation and dissociation functions within a common physical structure; other mass spectrometer systems may utilize separate structures for mass analysis and dissociation. For example, in an alternative construction of mass spectrometer 100, a quadrupole mass filter may be provided for isolation of a precursor ion species. Controller 140 may be programmed or otherwise configured to adjust RF and resolving DC voltages applied to the quadrupole mass filter electrodes to establish an isolation window of selected width that encompasses the range of m/z values of the precursor ions to be isolated. A collision cell may be located downstream of the quadrupole mass filter to effect fragmentation of the selected precursor ions by collisionally activated dissociation (CAD). Mass analyzer 115 (and/or one or more dissociation devices external to mass analyzer 115) may be configured to dissociate ions by a selected one of a plurality of available dissociation techniques. In the present example, mass analyzer 130 may be controllably operable to dissociate ions by conventional CAD, by PQD (described in U.S. Pat. No. 6,949,743 to Schwartz, the entire disclosure of which is incorporated by reference), or by ETD (described in U.S. Patent Publication No. US2005/0199804 to Hunt et al., the entire disclosure of which is also incorporated by reference), used either alone or with a supplemental collisional activation, or with a non-dissociative charge-reducing reaction step, typically utilizing an ion-ion reaction such as PTR. As is described in U.S. Pat. No. 7,026,613 to Syka, the entire disclosure of which is incorporated by reference, charge-state independent axial confinement of ions for simultaneous trapping of analyte and reagent ions in a common region of a two-dimensional trap mass analyzer may be achieved by applying oscillatory voltages to end lenses 160 positioned adjacent to mass analyzer 115. The foregoing set of available dissociation types is intended merely as an example, and other implementations of the invention may utilize additional or different dissociation types, including but not limited to photodissociation (such as IRMPD and UV), high-energy C-trap dissociation (abbreviated as HCD and described, for example, in Macek et al., "The Serine/Threonine/Tyrosine Phosphoproteome of the Model Bacterium Bacillus subtilis", Molecular and Cellular Proteomics, vol. 6, pp. 697-707 (2007)), and surface-induced dissociation (SID). It will be recognized that for ETD, a suitable structure (not depicted in FIG. 1) will be provided for supplying reagent (e.g., fluoranthene) ions to the interior volume of the mass analyzer or dissociation device for reaction with the multiply charged analyte cations and produce product cations.

Embodiments of the present invention may utilize a high resolution/accurate mass (HRAM) mass analyzer, such as an orbital electrostatic trap (marketed by Thermo Fisher Scientific under the trademark "Orbitrap") for acquisition of MS and/or MS/MS spectra. For such embodiments, an HRAM mass analyzer may be added to mass spectrometer 100 such that the HRAM mass analyzer and ion trap mass analyzer are arranged in a hybrid architecture, or alternatively the HRAM mass analyzer may be substituted for the ion trap mass analyzer. As used herein, the term "HRAM" denotes a mass analyzer capable of operating with a resolving power (at m/z 200) of at least 50,000 and a mass accuracy of less than 5 ppm.

Mass analyzer 115 and other components of mass spectrometer 100 are in electronic communication with a controller 140, which includes hardware and/or software logic for performing the data analysis and control functions described below. Controller 140 may be implemented in any suitable form, such as one or a combination of specialized or general purpose processors, field-programmable gate arrays, and application-specific circuitry. In operation, controller 140 effects desired functions of mass spectrometer 100 (e.g., analytical scans, isolation, and dissociation) by adjusting voltages applied to the various electrodes of mass analyzer 115 by RF, DC and AC voltage sources 145, and also receives and processes signals, from detectors 160, representative of mass spectra. As will be discussed in further detail below, controller 140 may be additionally configured to store and run data-dependent methods in which output actions are selected and executed in real time based on the application of input criteria to the acquired mass spectral data. The data-dependent methods, as well as the other control and data analysis functions, will typically be encoded in software or firmware instructions executed by controller 140.

In an embodiment, the instrument operator defines the data-dependent methods by specifying (via, for example, a command script or a graphical user interface) the input criteria (as used herein, references to "criteria" are intended to include an instance where a single criterion is utilized), output action(s), and the relationship between the input criteria and the output action(s). In a simple example, the operator may define a data-dependent method in which MS/MS analysis is automatically performed on the three ion-species exhibiting the greatest intensities in the MS spectrum. As discussed above, data-dependent methods of this type are known in the art.

Figures 2A, 2H:
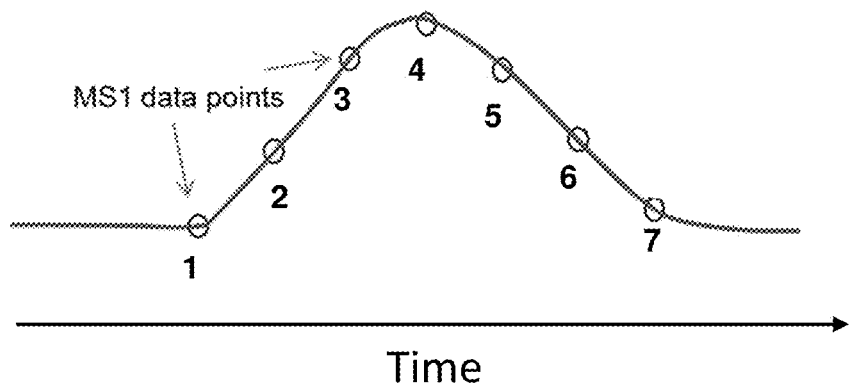
FIG. 2A shows the temporal locations of MS1 data-collection events, indicated by points 1-7, during the elution of a chromatographic peak.
FIG. 2H is a legend showing the meaning of the line widths, line lengths and arrows that are used to summarize the instrumental parameters in FIG. 2G.

A variable Data Dependent Acquisition and Dynamic Exclusion (vDDA-DE) experiment, in accordance with an embodiment of the present invention, will now be described with reference to FIGS. 2A-2H. Referring first to FIG. 2A, shown is a simplified chromatographic peak corresponding to a sample being eluted from a liquid chromatography column (e.g., a HPLC column). The average chromatographic peak-width defines a global cycle time, during which a plurality of independent vDDA cycles are performed. More particularly, in the instant embodiment at least seven vDDA cycles are performed within each global cycle in order to ensure sufficient MS1 data points for reproducible sample quantitation, but optionally the method is altered to fit user-defined requirements. By way of an example, five vDDA cycles may be employed if MS quantitation is not a requirement.

Each vDDA cycle within the global cycle includes a MS1 survey scan, which has a user-defined precursor mass range, as well as a set of tandem mass spectra (defined as the "loop count"). The loop count is variable, being determined in real-time based on the acquisition parameters employed and user-defined settings. As an example, if the average chromatographic peak width is determined to be 20 seconds, then each independent vDDA cycle can last only 2.9 seconds in order to support seven independent vDDA cycles during the global cycle. Since acquiring the MS1 survey scan requires ca. 350 msec, and assuming that the resolution is set to 140K, then approximately 2.65 seconds is available to be divided amongst the DDA scan events during each of the seven independent vDDA cycles.

Figure 2B:
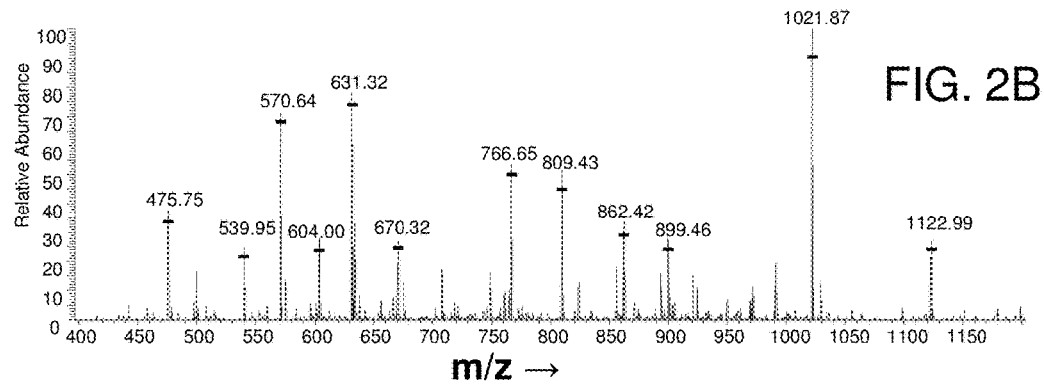
FIG. 2B shows a MS1 survey spectrum obtained at the start of a first vDDA cycle, with first indicators positioned above a first plurality of spectral peaks selected for MS/MS analysis.

Each one of the FIGS. 2B-2F corresponds to a different one of the first five vDDA cycles within the global cycle, the last two vDDA cycles being omitted from this discussion in the interest of brevity. More particularly, FIG. 2B corresponds to a first vDDA cycle beginning at point 1 in FIG. 2A, FIG. 2C corresponds to a second vDDA cycle beginning at point 2 in FIG. 2A, and so on. The full scan MS1 spectrum that is acquired at the beginning of the first vDDA cycle is shown in FIG. 2B, with indicators in the form of horizontal lines denoting the specific precursor m/z ranges selected for vDDA acquisition during the first vDDA cycle. Similarly, the full scan MS1 spectrum that is acquired at the beginning of each one of the second through fifth vDDA cycles is shown in FIGS. 2C through 2F, respectively, with indicators in the form of horizontal lines denoting the specific precursor m/z ranges selected for vDDA acquisition during each respective vDDA cycle.

Figure 2C:
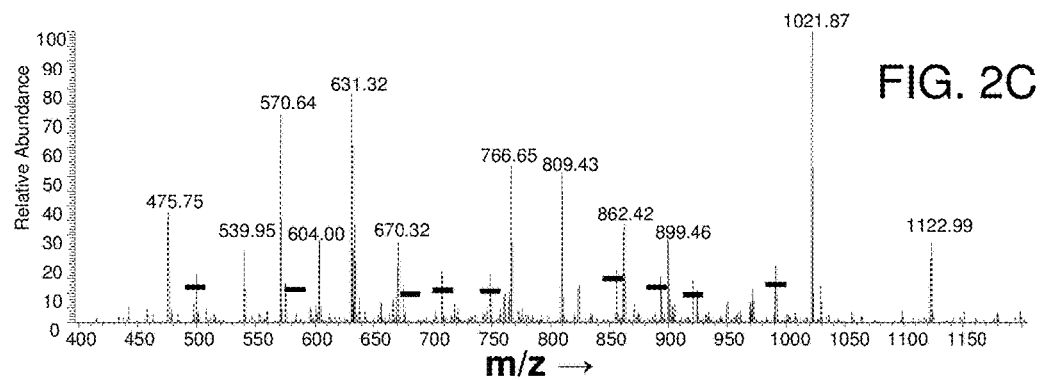
FIG. 2C shows a MS1 survey spectrum obtained at the start of a second vDDA cycle, with second indicators positioned above a second plurality of spectral peaks selected for MS/MS analysis.
Figure 2D:
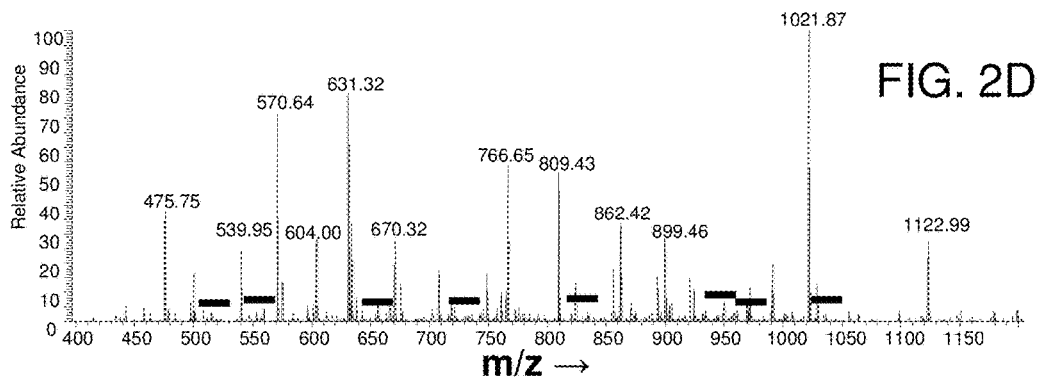
FIG. 2D shows a MS1 survey spectrum obtained at the start of a third vDDA cycle, with third indicators positioned above a third plurality of spectral peaks that have been selected for MS/MS analysis.
Figure 2E:
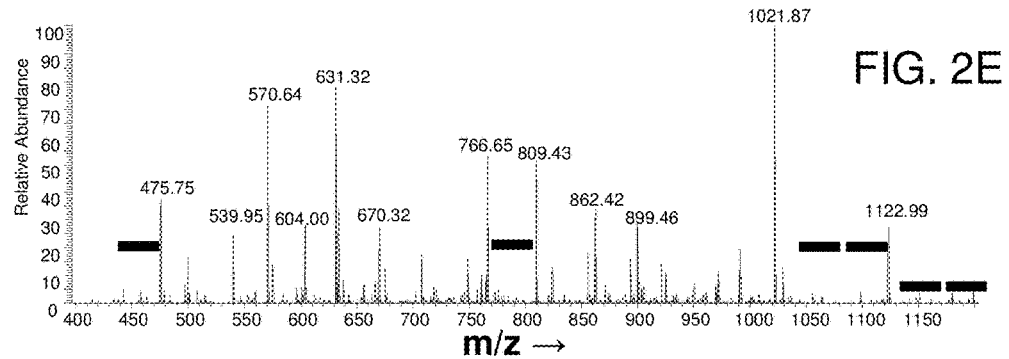
FIG. 2E shows a MS1 survey spectrum obtained at the start of a fourth vDDA cycle, with fourth indicators positioned above a fourth plurality of spectral peaks that have been selected for MS/MS analysis.
Figure 2F:
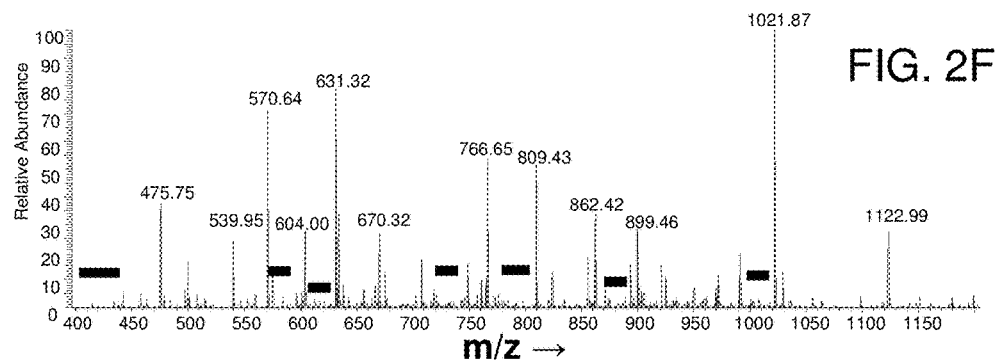
FIG. 2F shows a MS1 survey spectrum obtained at the start of a fifth vDDA cycle, with fifth indicators positioned above a fifth plurality of spectral peaks that have been selected for MS/MS analysis.

During the first vDDA cycle, beginning at point 1 in FIG. 2A, only those spectral peaks with relative abundances exceeding a first threshold value are selected for vDDA acquisition. The indicators shown in FIG. 2B are located above the selected spectral peaks, which in this specific example corresponds to the twelve highest relative abundance peaks in the MS1 spectrum. Similarly, during the second vDDA cycle only those spectral peaks with relative abundances between the first threshold value and a second threshold value are selected for vDDA acquisition. The indicators shown in FIG. 2C are located above the selected spectral peaks, which in this specific example corresponds to the next nine highest relative abundance peaks in the MS1 spectrum. The indicators shown in FIGS. 2D-2F are located above progressively lower relative abundance spectral peaks, which are selected for vDDA acquisition during the third through fifth vDDA cycles, respectively.

Figure 2G:
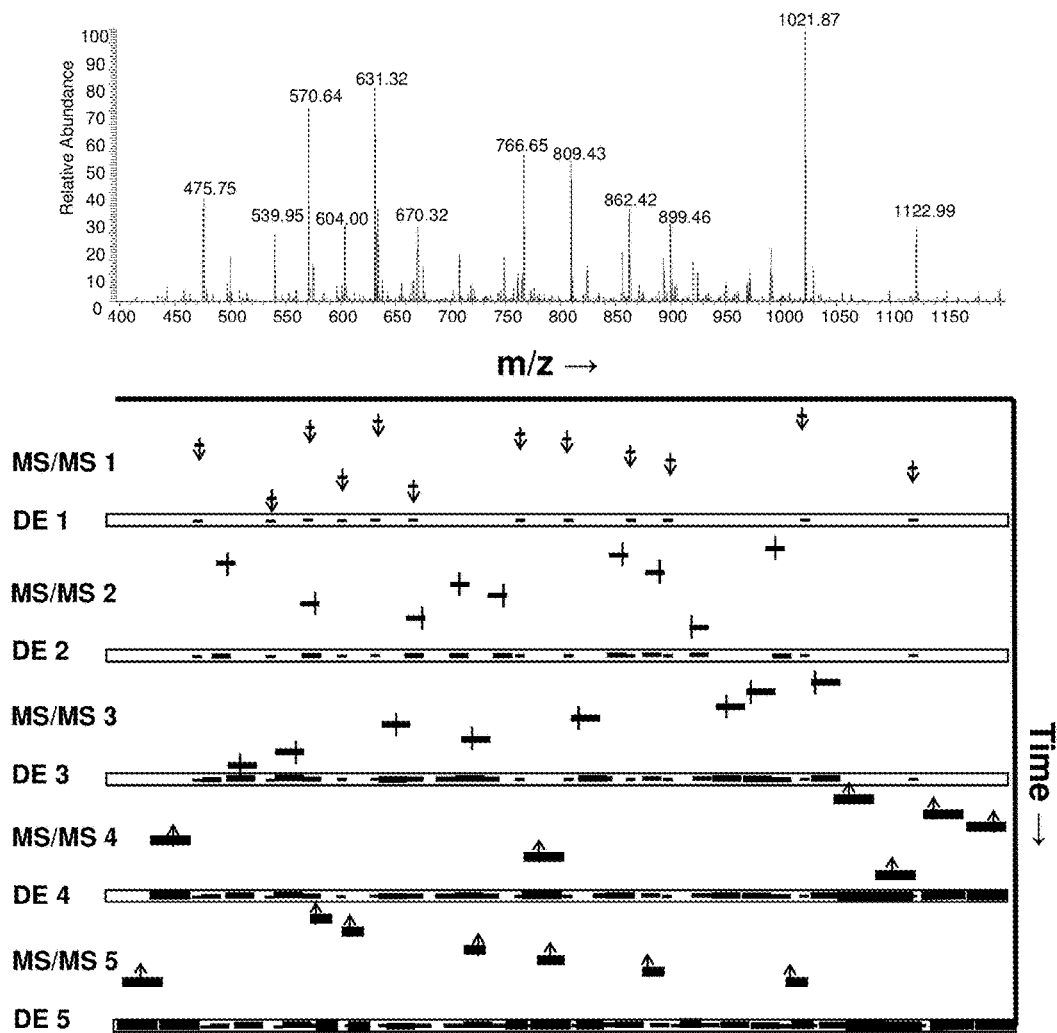
FIG. 2G reproduces the same MS1 survey spectrum that is shown in FIGS. 2B-2F (upper), and provides a summary of the MS/MS instrumental parameters that are employed during the first through fifth vDDA cycles as well as cumulative MS/MS spectral coverage achieved after each vDDA cycle (lower).

FIG. 2G illustrates the same MS1 survey spectrum that is shown in FIGS. 2B-2F (upper), and provides a summary of the MS/MS instrumental parameters that are employed during the first through fifth vDDA cycles, as well as the cumulative MS/MS spectral coverage that is achieved after each vDDA cycle (lower). Each of the indicators shown in the lower part of FIG. 2G denotes the specific combination of instrumental parameters used during the MS/MS analysis of each of the selected target precursors. Referring also to FIG. 2H, the length of the indicator line (short, medium-short, medium-long, long) represents the width of the precursor isolation window (2 Da, 5 Da, 10 Da, 15 Da, respectively), and the thickness of the indicator line (thin, medium, thick) represents the maximum ion fill time (30 ms, 80 ms, 150 ms, respectively). Additionally, a vertical line is used to denote the AGC target value, wherein a line with an arrowhead pointing up denotes the AGC target value 5e4, a line with no arrowheads denotes the AGC target value 1e5, and a line with an arrowhead pointing down denotes the AGC target value 5e5. The horizontal positions of the indicators in the lower portion of FIG. 2G are aligned with the positions of the corresponding spectral peaks in the MS1 survey spectrum. The vertical positions of the indicators in the lower portion of FIG. 2G are representative of the time-order in which different precursor m/z ranges are subjected to vDDA acquisition.

As will be apparent to a person having ordinary skill in the art, unlike prior DDA methods the instrumental parameters are not static in the present embodiment, but rather the precursor isolation width, the maximum ion fill time and the AGC target value may be determined "on the fly" so as to optimize MS/MS data collection. Generally speaking, the vDDA scan events acquired early in the global cycle, which target relatively higher relative abundance precursors (for example all precursors at least 50% relative abundance), are acquired using relatively narrow precursor isolation widths and relatively low AGC target values, resulting in faster tandem mass spectral acquisition, which in turn supports a higher loop count. On the other hand, the vDDA scan events acquired later in the global cycle, which target relatively lower relative abundance precursors (10-50% relative abundance), require relatively longer ion fill times prior to tandem mass spectral data acquisition, and thus lower loop counts are supported. Wider quadrupole precursor isolation windows, particularly for the vDDA scan events acquired later in the global cycle, can be utilized to sample a greater number of precursors per DDA scan event. Additionally, the max ion fill time can be extended to increase the S/N for the resulting chimeric product ion spectra. Of course, the actual quadrupole precursor isolation windows, maximum ion fill times and AGC target values are determined based on the precursor ion topology corresponding to the sample that is under investigation, which may dictate e.g., the use of wider quadrupole precursor isolation windows relatively early in the global cycle and/or narrower quadrupole precursor isolation windows relatively later in the global cycle, etc.

The lower portion of FIG. 2G also shows a cumulative dynamic exclusion (DE) topography after each of the DDA acquisition rounds (DE 1, DE 2, etc.). The DE topography is used to coordinate the selection of precursor m/z ranges for a next vDDA round. Therefore, DE 1 shows the DE topography associated with only the vDDA events in the first vDDA cycle, DE 2 shows the DE topography associated with vDDA events in the first two vDDA cycles, and so on. In practice, the entire quadrupole precursor isolation mass range is added to the DE list. As is illustrated in FIG. 2G, which shows only the first five of the seven vDDA cycles in the global cycle, performing multiple vDDA cycles facilitates the acquisition of at least one MS/MS data point covering every precursor m/z value in the user-defined MS window. This is achieved by using mass isolation windows of different widths for different target precursor m/z values, and by defining at least some of the mass isolation windows asymmetrically with respect to the target precursor m/z value. By defining asymmetric mass isolation windows, it is possible to reduce the extent of overlap with previously analyzed portions of the mass range of interest and cover the mass range of interest more effectively. In the example that is illustrated in FIG. 2G the aggregated coverage of the mass isolation windows is approximately 100% of the mass range of interest. In general, at least 70% coverage of the mass range of interest is achieved during the global cycle, and preferably at least 80-90% coverage of the mass range of interest is achieved during the global cycle.

For simplicity, the same MS1 spectrum has been shown in each one of FIGS. 2B-2G. Since the MS1 spectrum does not change during the global cycle in this simplified case, each successive vDDA cycle merely targets a set of spectral peaks having the next highest relative abundances. For this reason, it is not necessary to perform MS/MS analysis for any m/z range that has already been analyzed during an earlier vDDA cycle. As a result, the cumulative dynamic exclusion (DE) topography shown in FIG. 2G approaches 100% coverage relatively quickly.

In practice, the composition of the eluate may vary during the global cycle and therefore the MS1 survey spectra that are acquired at the beginning of the vDDA cycles early in the global cycle may differ from the MS1 survey spectra that are acquired at the beginning of vDDA cycles later in the global cycle. For this reason, the mass isolation windows are added to the DE list for a user-defined period of time that is less than the duration of the entire global cycle, such as for instance ca. 60% of the global cycle (i.e., about 12 seconds assuming a 20 second chromatographic peak width). When the limited exclusion period expires for a particular mass isolation window, it is removed from the DE list and then becomes available once again. Thus, a spectral peak around m/z 748 may trigger MS/MS acquisition during the second vDDA cycle with a 5 DA wide and symmetric isolation window, resulting in the mass range 745.5-750.5 being placed on the DE list. As the composition of the eluate changes during the global cycle, it is possible that a not illustrated spectral peak around m/z 749 may appear with a high relative abundance. Since m/z 749 falls within a mass range (i.e., 745.5-750.5) that has been added to the DE list during a previous vDDA cycle, the new peak at m/z 749 will not be selected as a target precursor ion until sufficient time passes and the mass range 745.5-750.5 becomes available again.

Figure 3:
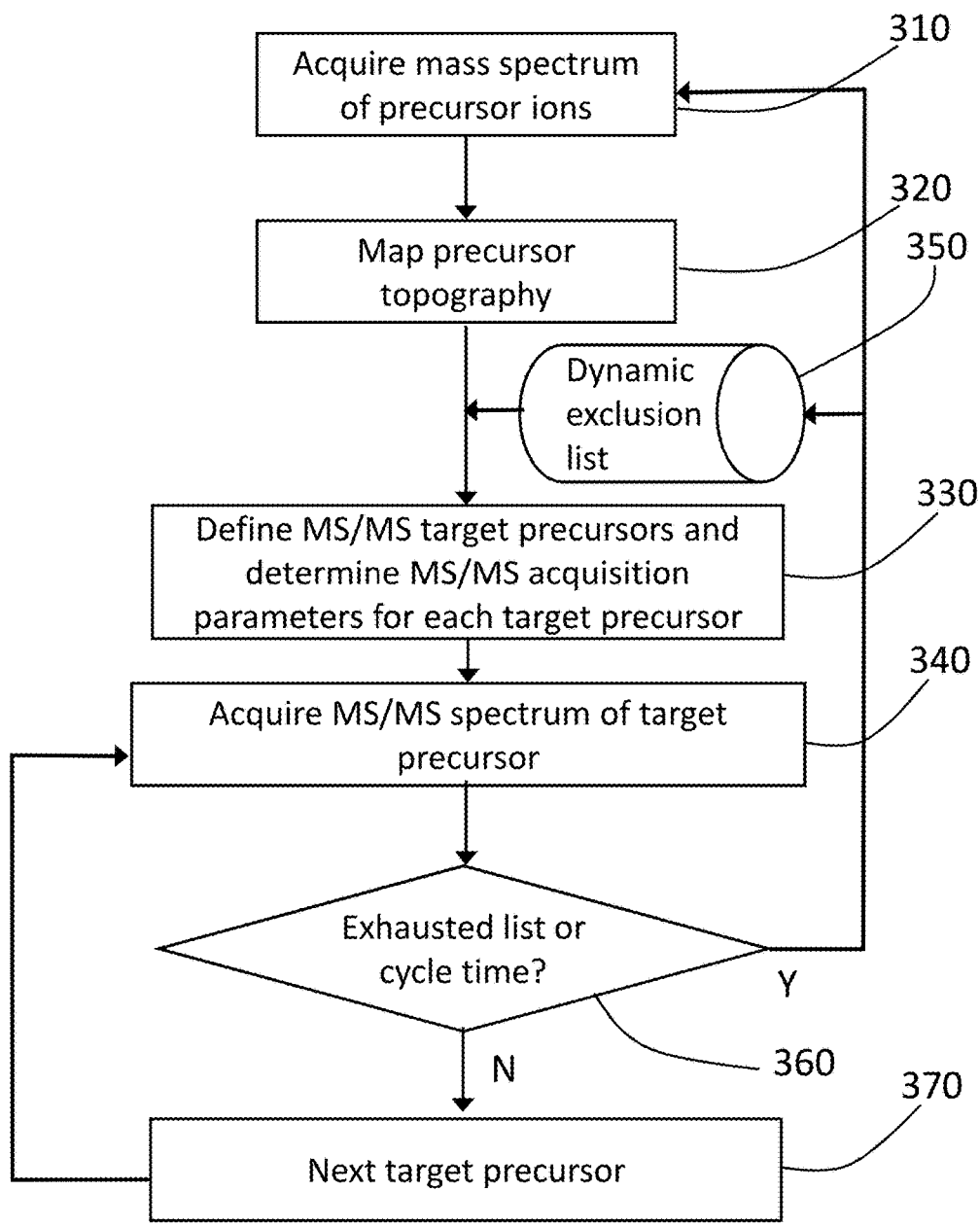
FIG. 3 shows the steps performed during a vDDA cycle.

Referring now to FIG. 3, shown is a simplified flow diagram outlining the steps that are performed during a single vDDA cycle. The steps may be implemented e.g. as a set of software instructions executed on one or more processors associated with controller 140 of the mass spectrometer system that is illustrated in FIG. 1. In order to ensure sufficient MS1 data points for reproducible quantitation, at least seven vDDA cycles are performed. Alternatively, fewer than seven vDDA cycles may be performed in some specific implementations.

In a first step 310, data representative of a mass spectrum of analyte ions is acquired by operation of a mass analyzer, such as by mass-sequentially ejecting ions from the interior of ion trap mass analyzer 115 to detectors 150. The mass spectrum is acquired over a user-defined mass range of interest. Although reference is made herein to "mass" analyzers and "mass" spectra, in a shorthand manner consistent with industry usage of these terms, one of ordinary skill in the mass spectrometry art will recognize that the acquired data represents the mass-to-charge ratios (m/z's) of molecules in the analyte, rather than their molecular masses. As is known in the art, the mass spectrum is a representation of the ion intensity observed at each acquired value of m/z. Standard filtering and preprocessing tools may be applied to the mass spectrum data to reduce noise and otherwise facilitate analysis of the mass spectrum. Preprocessing of the mass spectrum may include the execution of algorithms to assign charge states to m/z peaks in the mass spectrum, utilizing a known algorithm for charge state determination.

Precursor target ion selection for subsequent MS/MS analysis utilizes a MS1 precursor topography map, which is generated at step 320. After the MS1 spectrum of the mass range of interest has been collected, a process in execution on the one or more processors of controller 140 identifies precursor m/z features therein, including: i) precursor isotopic clusters to determine charge states, ii) measured ion intensities, and iii) ion flux for potential precursor m/z targets. Existing dynamic exclusion features (if any) are then retrieved, including: i) precursor m/z features (i.e., m/z values and isotopic clusters), ii) isolation windows, and iii) the current exclusion duration time.

At step 330 a list of precursor targets is determined for the current vDDA cycle. Additionally, a set of MS/MS acquisition parameters is determined for each precursor target on the list. The step of determining the MS/MS acquisition parameters includes firstly determining the target precursor m/z value (step 320). The precursor topography is then evaluated to set the precursor isolation window for the subsequent MS/MS acquisition parameters. Evaluating the precursor topography includes: i) determining the relative abundance value of the target precursor m/z value, ii) reading in the existing dynamic exclusion list, iii) determining the available isolation window (symmetrical/asymmetrical), and iv) determining the degree of overlap with previous MS/MS events. The instrument MS/MS acquisition parameters are then set, including: i) setting the automatic gain control (AGC) target value, ii) setting the ion accumulation time, and iii) matching the MS/MS resolution setting with the maximum ion fill time.

At step 340 the MS/MS spectrum of one of the target precursors on the list for the current vDDA cycle is acquired, utilizing the MS/MS acquisition parameters that were defined during the previous step. Optionally, the MS/MS spectrum is a high resolution accurate mass (HRAM) MS/MS spectrum of the one of the targeted precursors.

At decision step 360, it is decided if the target precursor list for the current vDDA cycle is exhausted or if the current vDDA cycle time has elapsed. If no, then the method moves on to the next target precursor at step 370, and the method loops back to step 340. The MS/MS spectrum of the next targeted precursor is then acquired, utilizing the MS/MS acquisition parameters that were defined at step 330 for the next targeted precursor m/z. If yes, then the method loops back from step 360 to step 310, the dynamic exclusion list is updated at step 350, and the next MS1 spectrum is acquired to start the next vDDA cycle. More particularly, the entire isolation window of m/z values determined for each of the target precursors for the current vDDA cycle is added to the dynamic exclusion list at step 350.

The vDDA/DE method described above with reference to FIG. 3 leverages the concepts of DDA/DE to not only increase the range of precursor m/z values sampled in a chromatographic peak width, but to also increase the multiplex spectral quality. The full scan MS1 spectrum and existing DE list are used to determine the precursor m/z target, precursor isolation window, AGC setting, and ion fill times to offset limitations to intra-scan dynamic range associated with trapping instruments. In addition, at least some of the isolation windows can be asymmetrical with respect to the target precursor m/z values to avoid redundant precursor sampling, and thereby increase the overall MS/MS coverage. Once the precursor m/z isolation window is determined, all precursor signals can be recorded based on isotopic groupings (charge states and isotopes) to define subsequent precursor targets. The combined results increase precursor sampling within one sample as well as across all samples evaluated in the study.

For most chromatographic peak widths (20-30 seconds), the vDDA routine will sample the entire user-defined precursor mass range more than once during a global cycle to increase confidence in post-acquisition data processing. For UHPLC methods (peak widths<15 sec), the vDDA method can ensure at least one DDA event covering the user-defined precursor mass range.

In the implementation described above with reference to FIGS. 2A-H and FIG. 3, the vDDA/DE process uses the MS1 full scan to set parameters including the width of the mass isolation window, the symmetry/asymmetry of the mass isolation window, the AGC target, and the max ion fill time. The following examples illustrate additional non-limiting implementations of the vDDA/DE method described above.

EXAMPLE 1

In this first example the MS1 full scan is used not only to detect the precursor m/z range that is selected for tandem mass spectrometry, as is currently done by the DDA algorithm, but additionally to evaluate the relative abundance of all precursors in the m/z window of interest and to adjust the AGC target value, maximum ion fill time, and resolution setting accordingly. However, in each case the mass isolation window width is static and symmetrically centered on the selected precursor m/z value.

Figure 4:
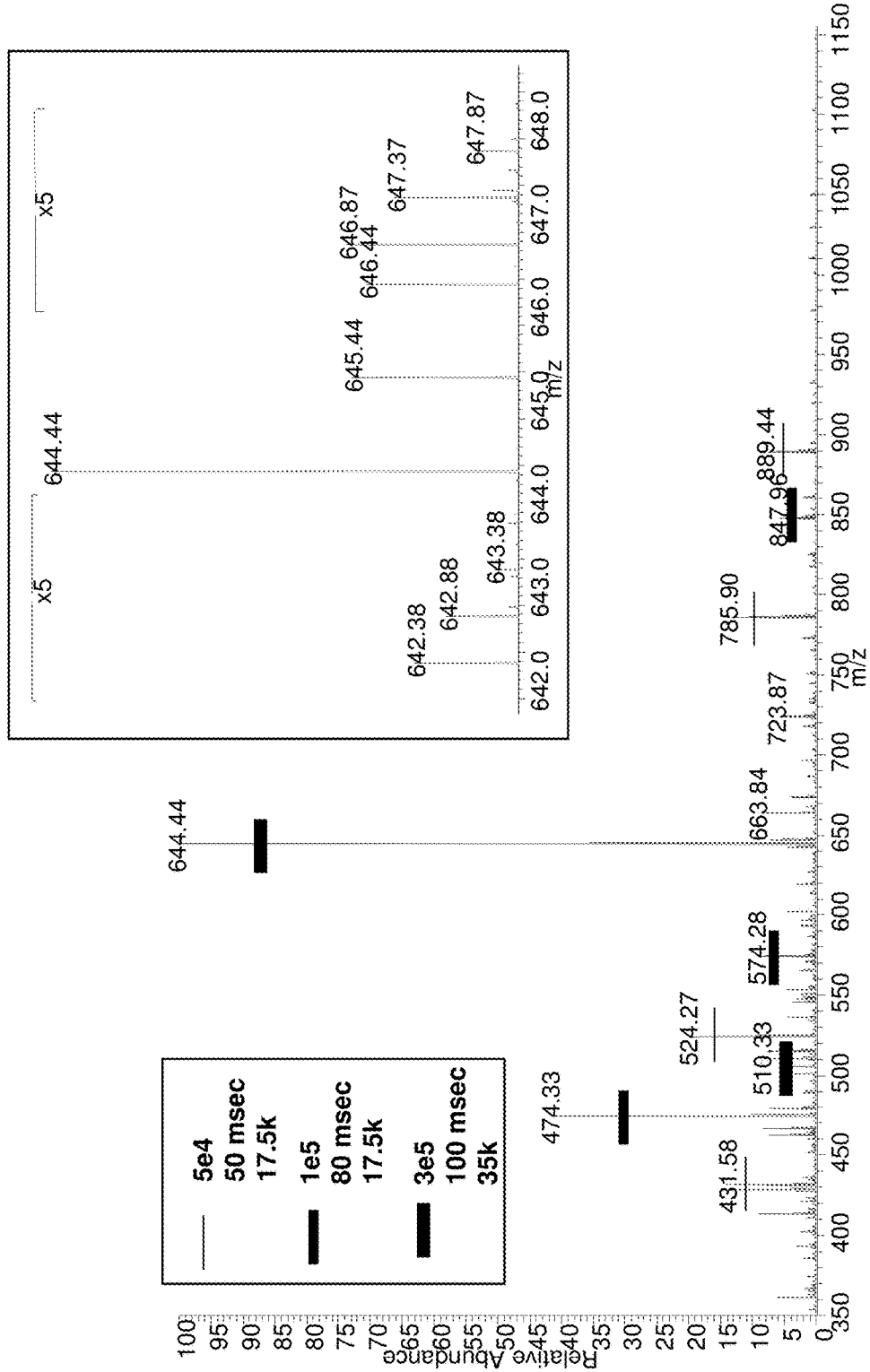
FIG. 4 shows a MS1 survey spectrum with different indicators positioned above different spectral peaks and denoting different instrumental parameters selected for performing MS/MS analysis of the ions corresponding to the different spectral peaks. The inset shows a narrow precursor mass range covering the base peak. The example parameters used to demonstrate variable DDA are specified in the legend.

FIG. 4 shows a plurality of plausible target precursors selected for subsequent DDA sequencing. Indicator lines of different thicknesses are used to represent the MS/MS acquisition parameters determined for each of the selected targets, but using a common precursor isolation window. Example MS/MS acquisition parameters are defined in the accompanying legend. As will be apparent, the different indicator line thicknesses represent different combinations of target AGC value, maximum ion fill time, and orbital electrostatic trap (Orbitrap) resolving power used for tandem mass spectral data acquisition.

For a precursor m/z range with a very abundant precursor, the AGC value is set to 3e5 to reduce ion suppression of product ions from low-level precursors simultaneously isolated and dissociated (typical AGC setting is 5e4 on the Q Exactive mass spectrometer). The assumption is that isolation windows containing multiple precursor isotopic clusters with large dynamic ranges require higher AGC target settings and longer fill times to increase the probability of reliably measuring product ions from the less abundant precursor. The inset box shown in FIG. 4 illustrates a narrow precursor m/z range around the base peak, with the m/z ranges to the left and right of the base peak being magnified to display low-level precursors. The two sets of isotopic clusters (m/z 642.38 and 646.44) have a relative abundance of ca. 2% as compared to the m/z 644 precursor. The resulting chimeric product ion spectra would contain product ions with similar relative abundance as that in the MS spectrum and with a low AGC setting (5e4), ion statistics reduce the probability of successfully and confidently identifying each peptide based on spectral matching.

For lower level precursors (e.g., the marked precursor range centered on m/z 524.27) the standard MS/MS parameters can be used as there is neither high density of precursors in the 10 Da quadrupole isolation window or large differences in the measured ion intensities. Therefore, a short acquisition time would be needed to acquire a meaningful product ion spectrum. The last situation outlined in FIG. 4 is represented by the precursor isolation window centered at m/z 474.33. There would be multiple precursors co-isolated in the scan event and a 20% difference in measured ion abundance values.

EXAMPLE 2

In this second example the routine DDA/DE selection process is utilized to define the static quadrupole precursor isolation window, but asymmetric boundaries are set around the specific precursor. The routine DDA/DE process selects m/z values based on either the most or least abundant ions based on intensity. The precursor isolation width is then dictated by the user settings (e.g. 2, 5, 8, 10 Da values) centered on the precursor m/z value. User-defined options enable either the precursor m/z value or the mass width used for isolation to be stored in the DE table for user-specified time to avoid resampling the same precursor window, but does not enable asymmetric windows to be used.

Figure 5:
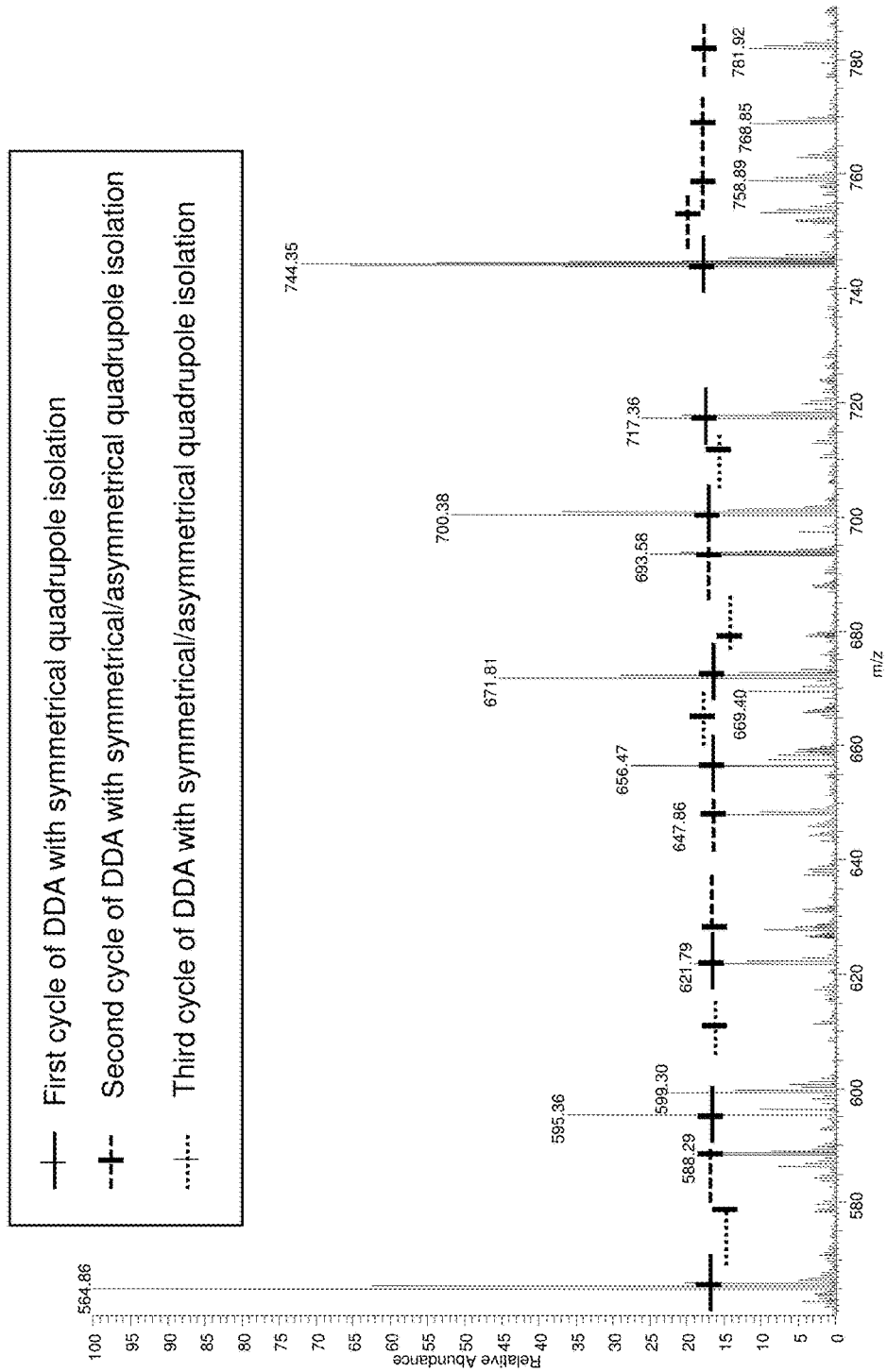
FIG. 5 shows a MS1 survey spectrum, with different indicators positioned above different spectral peaks, showing the mass range coverage that is achieved after three cycles of vDDA using both symmetrical and non-symmetrical quadrupole isolation windows of uniform width.

Referring now to FIG. 5, three DDA cycles are performed using a combination of symmetric and asymmetric isolation windows. The first cycle of tandem mass spectral acquisition (solid lines) utilizes static precursor isolation sizes symmetrically centered on the target precursor m/z value as marked by the vertical line. The entire precursor m/z range sampled by each tandem mass spectrum during the first DDA cycle is recorded in the DE table. Subsequent DDA cycles (dashed lines) may trigger a precursor that has not been previously sampled but that is close to a precursor mass range sampled within the DE duration. For example, FIG. 5 shows m/z 588 was not isolated in the tandem mass spectral event centered on m/z 595, but the symmetric precursor isolation window covered up to m/z 590. Therefore, the vDDA quadrupole isolation setting targeting m/z 588 may be selected to begin at m/z 581 and end at 591 (1 Da overlap with an existing DDA window). The asymmetrical precursor isolation window would not only sample the precursor at m/z 588, but also the precursor at m/z 585 and remove it from consideration for subsequent DDA events. The use of symmetrical and asymmetrical precursor isolation windows facilitates high MS/MS coverage of the mass range of interest. Optionally, the tandem mass spectral settings (e.g., AGC target value, max ion fill time, resolving power, etc.) are variable, as described above.

EXAMPLE 3

This third example leverages variable acquisition parameters for all aspects of tandem mass spectral acquisition, including the quadrupole isolation event to sample the user-defined precursor m/z range in one, two, or three DDA cycles. The goal is to effectively sample the entire precursor m/z range multiple times across every chromatographic peak width. For trapping instruments, charge density becomes a limiting factor to detect product ions from low-level precursors in the presence of more abundant precursors. This limitation is due to intra-scan dynamic range associated with trapping instruments. There are two options to increase product ion detection of two precursors that are separated by narrow m/z values—acquire two different tandem mass spectra for each, or increase the charge density through AGC (and ion fill time). The latter option was described above. The former option is performed when the MS topography is defined and high abundant precursors are identified, the quadrupole isolation window can be significantly reduced to 2 Da to reduce the negative effects of low-level product ion suppression, whereas regions of the MS topography with equally abundant (or sparsely populated) regions have much wider quadrupole precursor isolation windows.

Figure 6:
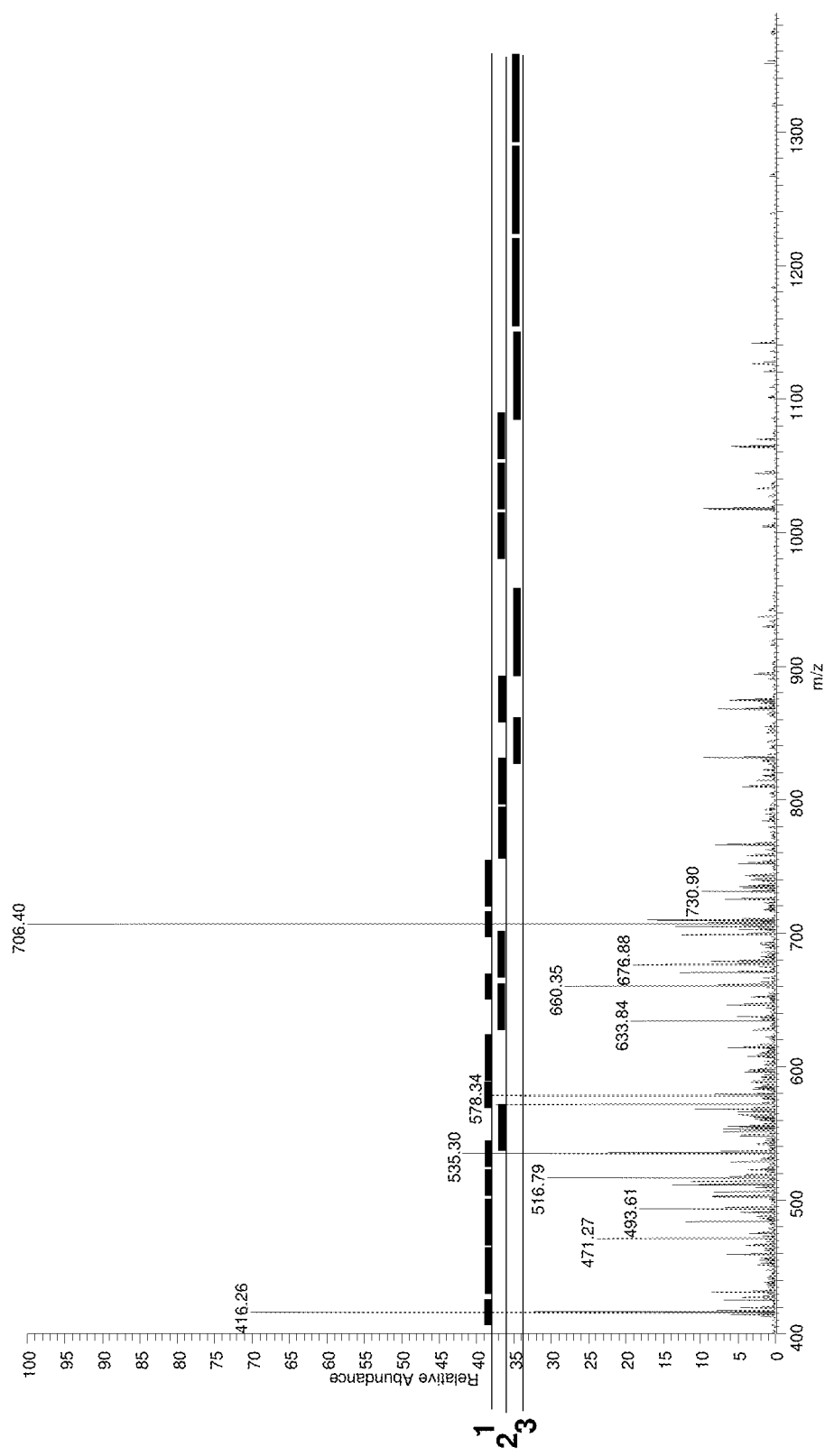
FIG. 6 illustrates a MS1 survey spectrum, with different indicators positioned above different spectral peaks, showing aggregate coverage of the mass spectral range of interest after three cycles of vDDA using quadrupole isolation windows of various widths.

Referring now to FIG. 6, variable quadrupole precursor isolation windows (and other MS/MS acquisition parameters) are used for rapid sampling of the precursor m/z range. The lengths of the horizontal line indicators are proportional to the window size, and the numbers 1, 2 and 3 denote the DDA cycle within which each of the sets of MS/MS events is acquired. A total of 26 DDA events are shown the on MS spectrum to cover a precursor m/z range of ca. 1000 Da (m/z 400-1400).

The example presented only has three different cycles, but algorithms could be created to evaluate the precursor topography and determine the windows used to sample the entire user-defined precursor mass range in 2 vDDA cycles, or to expand the example presented in FIG. 6 to the subsequent 4-7 DDA cycles as based on the ratio of acquisition cycle time and average chromatographic peak width. Based on the average peak width, the isolation windows could be as large as 20-30 Da if there are few precursors measured. As described above, either longer ion fill times or higher AGC settings could be used to increase the quality of the chimeric spectra for subsequent data processing. The described process facilitates multiple MS/MS events per precursor m/z range under the chromatographic elution profile for increased sequence confidence, increases capabilities to determine putative matrix interference, and also facilitates extremely high peak capacity from ultra-high performance liquid chromatography (UHPLC) separations to enable one MS/MS event per precursor m/z value.

EXAMPLE 4

This fourth example addresses the requirement for fast cycle time and combines the vDDA window concept with the most efficient cycle time. In this case, the user determines a fixed cycle time, e.g. 1.5 sec and the total number of DDA events that should be accomplished within the cycle time of 1.5 sec. The vDDA algorithm then assesses the precursor topology in the MS1 scan and calculates the specified number of DDA events with a fixed window around the most intense precursor ions. If the number of DDA events with fixed precursor events adds to less than 1.5 seconds the method proceeds to acquire DDA runs, but utilizes the remaining time in the cycle to acquire one or several MS2 events with wider windows using the vDDA concept described above. The algorithm finds an optimal trade-off between prioritizing DDA events with narrow isolation windows (best and most efficient method to obtain solid identifications through MS/MS database searching) with the wider isolation windows in other areas with less intense ions that can be combined to achieve complete coverage over the entire desired mass range. This decision can be made intensity dependent and with asymmetric windows as described above in the first and second examples. A specific requirement for this vDDA method is that the entire mass range is completely acquired for every duty cycle to provide a complete "record" of the MS/MS fragments generated during the duty cycle.

EXAMPLE 5

This fifth example implementation combines the vDDA concept described above with the capability of extending the quadrupole precursor isolation windows to facilitate partial overlap with existing DDA scan events. For example, within one global acquisition cycle, there can be a recorded vDDA spectrum that isolated the precursor m/z range of 500-510 Da and a subsequent vDDA event is triggered on m/z 512. A 10 Da precursor isolation window centered on m/z 510 (covering m/z 505 to 515) can be acquired. Resulting data processing can evaluate the multiple product ion spectra that may contain a precursor m/z value (as determined from the knowledge base) and compare the potential product ion distribution overlap with the reference spectrum (spectral matching routine) and utilize the multiple scores for increased confirmation.

EXAMPLE 6

Figure 7:
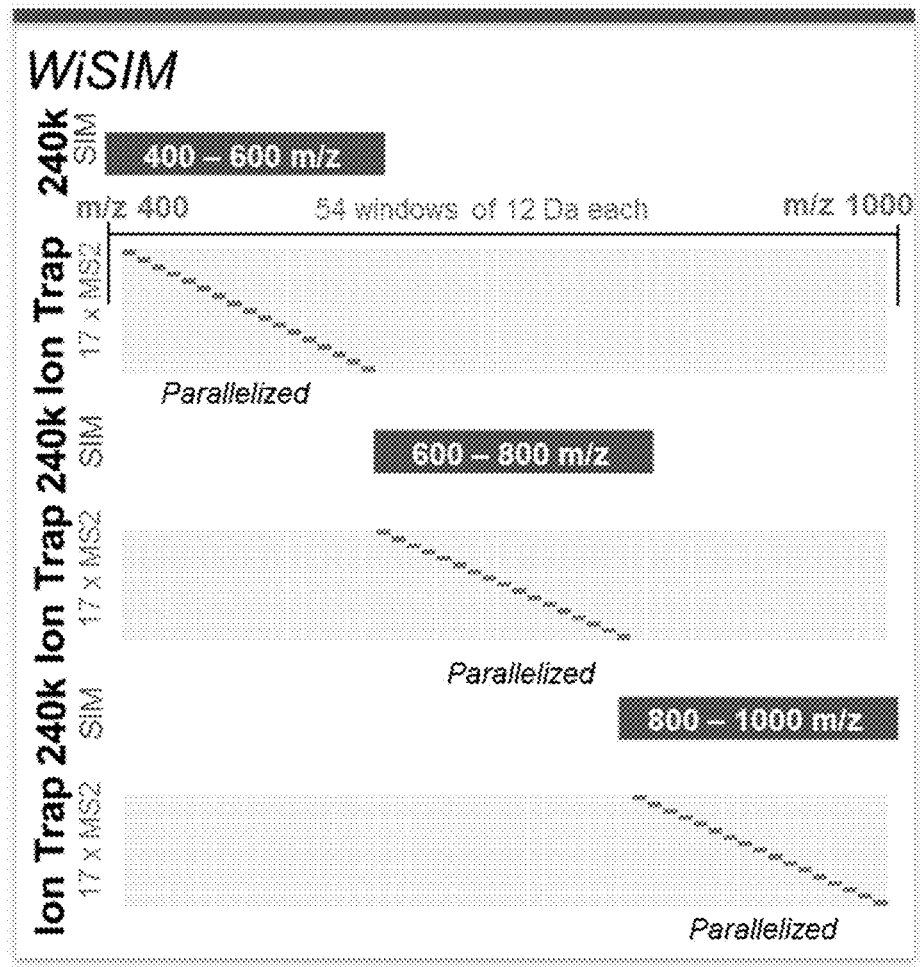
FIG. 7 illustrates WiSIM data.

This sixth example implementation combines the vDDA concept described above with the MS1-based gas phase fractionation approach described in the WiSIM method. The entire mass range of interest is covered in two or multiple SIM steps to achieve a complete duty cycle that covers the entire mass range. FIG. 7. shows the main concept of MS1 gas phase fractionation which can be used in combination with the vDDA concept to maximize the dynamic range for the MS1 quantitation and take advantage of the high MS2 dynamic range and complete coverage provided by the vDDA approach.

The foregoing description of methods and embodiments of the invention has been presented for purposes of illustration. It is not intended to be exhaustive or to limit the invention to the precise steps and/or forms disclosed, and many modifications and variations are possible in light of the above teaching. It is intended that the scope of the invention and all equivalents be defined by the claims appended hereto.

What is claimed is:

1. A method for mass spectral analysis of a sample containing a plurality of biomolecule species, comprising performing a global acquisition cycle having a plurality of data-dependent acquisition cycles across a chromatographic elution peak, each data-dependent acquisition cycle including steps of:
   a. acquiring a survey MS1 scan extending across a mass range of interest of an ensemble of ions generated from a sample;
   b. selecting a plurality of precursor ions in the survey MS1 scan that exceed an intensity threshold, the selected plurality of precursor ions excluding precursor ions selected in previous data-dependent acquisition cycles, the intensity threshold being lower than an intensity threshold of a previous data-dependent cycle in the same global acquisition cycle; and
   c. for each of the plurality of selected precursor ions, isolating ions having m/z values within a precursor isolation window, the precursor isolation window having a width, fragmenting the isolated ions, and mass analyzing the fragmented isolated ions to generate a MS/MS spectrum, wherein the precursor isolation window width is larger than a precursor isolation window width of a previous data-dependent cycle in the same global acquisition cycle.

2. The method of claim 1, wherein the selected plurality of precursor ions further excludes precursor ions having a mass-to-charge (m/z) value that falls within a range of m/z values encompassed by the isolation window used during the acquisition of the MS/MS spectrum of one of the target precursors selected in a previous data-dependent acquisition cycle.

3. The method of claim 1, further comprising determining, for each of the selected precursor ions, an instrumental parameter including at least one of an automatic gain control (AGC) target value and a maximum ion fill time.

4. The method of claim 1, wherein the sample is eluted from a liquid chromatography column, and comprising performing at least seven data-dependent acquisition cycles during elution of the sample from the liquid chromatography column.

5. The method of claim 1, wherein at least one of the isolation windows is asymmetric with respect to the corresponding precursor ion.

6. The method of claim 1, wherein the aggregate coverage of the isolation windows for the global acquisition cycle is at least 70% of the mass range of interest.

7. The method of claim 1, further comprising, for each data-dependent acquisition cycle, adjusting at least one of: a number of selected precursor ions, and instrument parameters associated with the selected precursor ions, such that a duration of the data-dependent acquisition cycle does not exceed a prespecified maximum value.

8. The method of claim 1, wherein each isolation window is set so as to not encompass any previously selected precursor ions.

9. The method of claim 1, wherein the mass range of the survey scan is at least 10 Thomson.

10. The method of claim 1, wherein the step of acquiring the survey MS1 scan is performed using a mass analyzer operating at a resolving power of at least 50,000.

11. The method of claim 10, wherein the mass analyzer is an orbital trapping analyzer.

12. The method of claim 1, wherein at least one isolation window used in a data-dependent acquisition cycle is selected to overlap with an isolation window used in a prior data-dependent acquisition cycle in the same global acquisition cycle.

13. The method of claim 1, wherein the step of isolating ions having m/z values within a precursor isolation window is performed using a quadrupole mass filter.

14. The method of claim 1, wherein the step of fragmenting the isolated ions is performed by collisionally activated dissociation.

15. A method for mass spectral analysis of a sample containing a plurality of biomolecule species, comprising performing a global acquisition cycle having a plurality of data-dependent acquisition cycles across a chromatographic elution peak, the plurality of data-dependent cycles including a first data-dependent acquisition cycle and at least one subsequent data-dependent acquisition cycle, each data-dependent acquisition cycle including steps of:
   a. acquiring a survey MS1 scan extending across a mass range of interest of an ensemble of ions generated from a sample;
   b. selecting a plurality of precursor ions in the survey MS1 scan that exceed an intensity threshold, the selected plurality of precursor ions in the at least one subsequent data-dependent acquisition cycle excluding precursor ions selected in previous data-dependent acquisition cycles; and
   c. for each of the plurality of selected precursor ions, isolating ions having m/z values within a precursor isolation window, fragmenting the isolated ions, and mass analyzing the fragmented isolated ions to generate a MS/MS spectrum.
   wherein, during the first data-dependent acquisition cycle, the precursor isolation window for each of the selected precursor ions is symmetric with respect to the mass-to-charge ratio of the selected precursor ion; and
   wherein, during the at least one subsequent data-dependent-acquisition cycle, at least one precursor isolation window is asymmetric with respect to the mass-to-charge ratio of the selected precursor ion.

16. The method of claim 15, further comprising determining, for each of the selected precursor ions, an instrumental parameter including at least one of an automatic gain control (AGC) target value and a maximum ion fill time.

17. The method of claim 15, wherein the aggregate coverage of the isolation windows for the global acquisition cycle is at least 70% of the mass range of interest.

18. The method of claim 15, further comprising, for each data-dependent acquisition cycle, adjusting at least one of: a number of selected precursor ions, and instrument parameters associated with the selected precursor ions, such that a duration of the data-dependent acquisition cycle does not exceed a prespecified maximum value.

19. The method of claim 15, wherein each isolation window is set so as to not encompass any previously selected precursor ions.

20. The method of claim 15, wherein the step of acquiring the survey MS1 scan is performed using a mass analyzer operating at a resolving power of at least 50,000.

21. The method of claim 20, wherein the mass analyzer is an orbital trapping analyzer.

22. The method of claim 15, wherein at least one isolation window used in a subsequent data-dependent acquisition cycle is selected to overlap with an isolation window used in a prior data-dependent acquisition cycle in the same global acquisition cycle.

* * * * *